United States Patent [19]

Kinoshita

[11] Patent Number: 4,550,716
[45] Date of Patent: Nov. 5, 1985

[54] LIQUID SUPPLYING DEVICE FOR ENDOSCOPE

[75] Inventor: Kunio Kinoshita, Tokyo, Japan

[73] Assignee: Olympus Optical Company, Tokyo, Japan

[21] Appl. No.: 603,695

[22] Filed: Apr. 25, 1984

[30] Foreign Application Priority Data

Apr. 30, 1983 [JP] Japan .................................. 58-77327

[51] Int. Cl.⁴ .............................................. A61B 1/06
[52] U.S. Cl. ....................................................... 128/6
[58] Field of Search ........................................ 128/4, 6

[56] References Cited

U.S. PATENT DOCUMENTS

| | | | |
|---|---|---|---|
| 4,261,343 | 4/1981 | Ouchi et al. | 128/4 |
| 4,311,134 | 1/1982 | Mitsui et al. | 128/6 |
| 4,325,362 | 4/1982 | Ouchi et al. | 128/4 |
| 4,325,695 | 4/1982 | Ouchi et al. | |
| 4,402,310 | 9/1983 | Kimura | 128/4 |

*Primary Examiner*—William H. Grieb

[57] ABSTRACT

A liquid supplying device has a housing with a connecting portion to which a connector of an endoscope is connected. A lamp, an air pump and a liquid supply tank are arranged in the housing. The pump is connected to the connecting portion and the tank through a pipe. The tank is connected to the connecting portion through a pipe. A switching mechanism is connected to the pipes. A selector valve is connected to the pipe at a position between the pump and the tank. A control circuit is connected to the lamp and pump, and a light source switch is connected to the control circuit. When the switch is closed, the circuit drives the lamp and pump and switches the selector valve to a first position for blocking the pipe, thereby preventing supply of the liquid to the endoscope. When the switch is open, the circuit switches the selector valve to a second position for communicating the pipe. If the switching mechanism is operated under this condition, the liquid is supplied to the endoscope through the pipe.

12 Claims, 34 Drawing Figures

F I G. 9
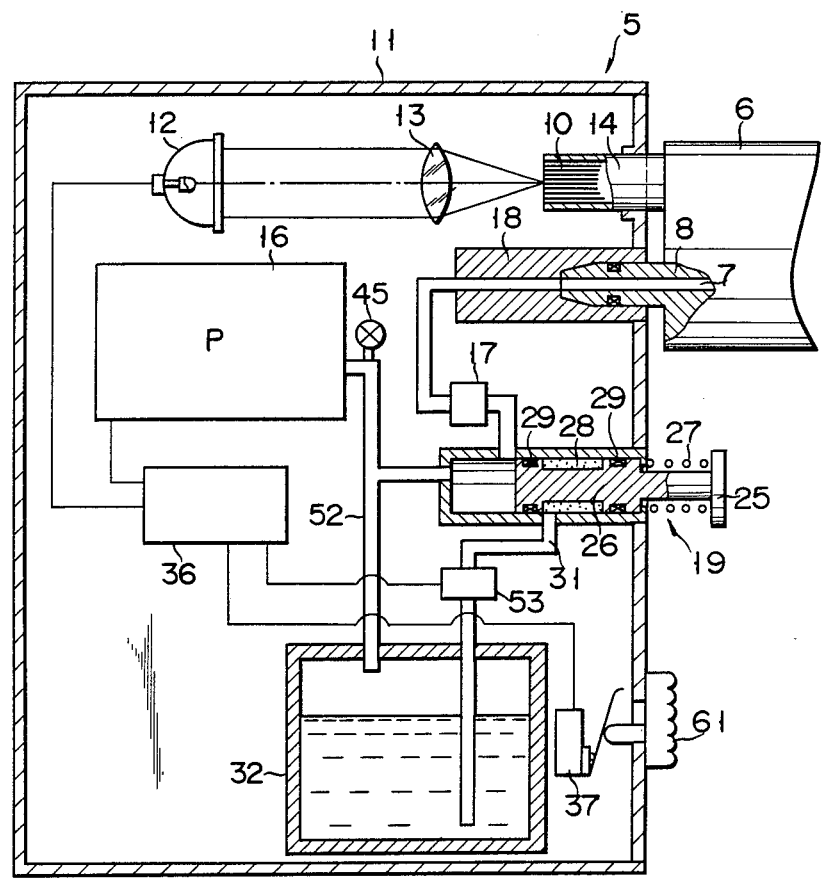

F I G. 17 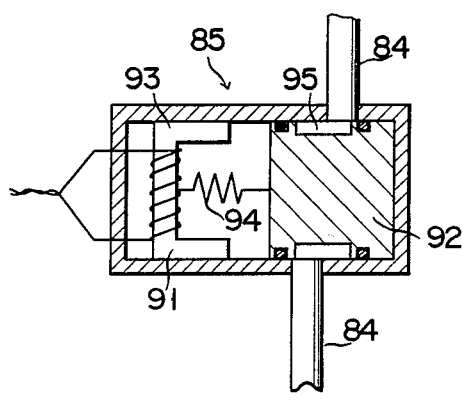 F I G. 18 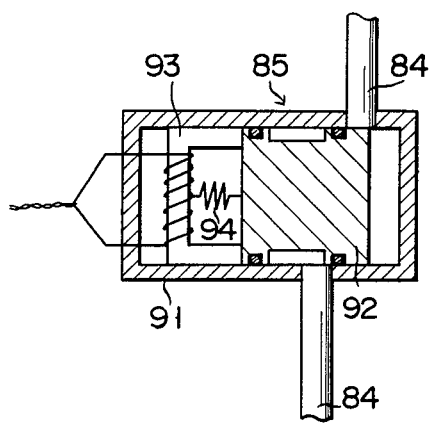
F I G. 19 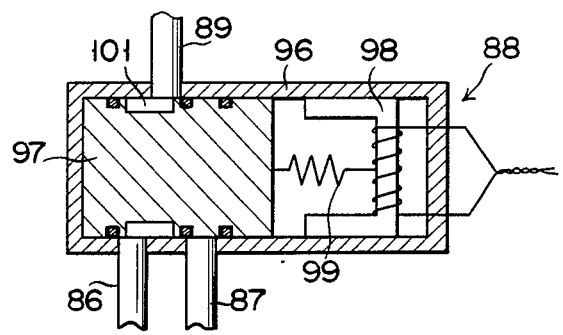
F I G. 20 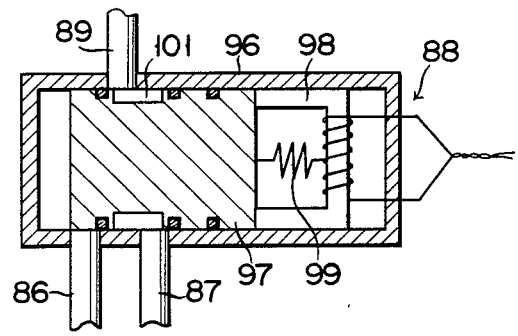

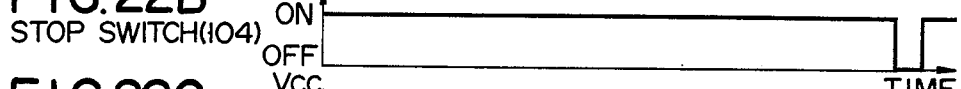
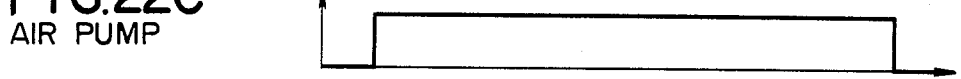
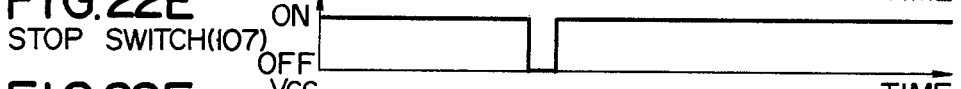
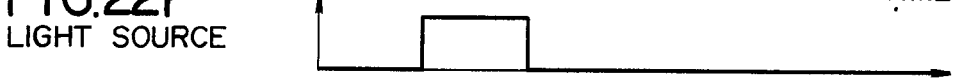
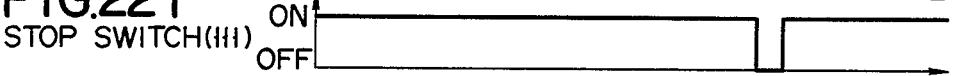
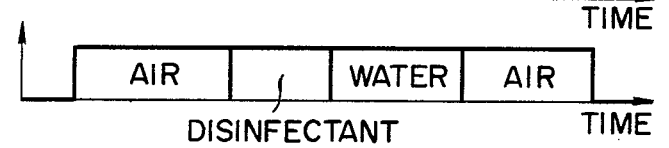

LIQUID SUPPLYING DEVICE FOR ENDOSCOPE

BACKGROUND OF THE INVENTION

The present invention relates to a liquid supplying device for supplying a liquid in an air supply channel of an endoscope so as to clean this air supply channel.

In order to prevent infection from an endoscope, a liquid supplying device is provided which can easily clean an air supply channel of an endoscope after use. This device is assembled in a light source of the endoscope. In this device, a switching mechanism is operated to selectively supply a liquid held in a liquid supply tank to an air supply channel of an endoscope. However, if the switching mechanism is accidentally operated during diagnosis with the endoscope connected thereto, a liquid, such as an infusion solution harmful to the human body, may be supplied to a patient undergoing diagnosis.

In order to prevent this, another liquid supply device has been proposed. According to this device, a light source connector and a liquid supply connector are arranged independently of each other. Therefore, even if a switching mechanism is accidentally operated during diagnosis with an endoscope connected thereto, a liquid will not be erroneously supplied to the patient. However, this device has a complex structure and its operation is difficult.

SUMMARY OF THE INVENTION

The present invention has been made in consideration of this and has as its object to provide a liquid supplying device in which a liquid cannot be supplied while an illuminating light source lamp is ON so as to guarantee the safety of a patient and which is easy to operate.

According to an aspect of the present invention, there is provided a liquid supplying device which comprises a housing with a connecting portion to which the connector of the endoscope is connected; air and liquid supplying means, arranged inside the housing, for supplying liquid and air into the air supply channel from the other end of the air supply channel; a light source which is arranged inside the housing and which emits light which becomes incident on the light guide from that end of the light guide which is near the connector; and regulating means for preventing the air and liquid supplying means from supplying liquid while said light source is ON.

BRIEF DESCRIPTION OF THE DRAWINGS

FIG. 9 is a sectional view showing a liquid supplying device according to a third embodiment of the present invention;

FIGS. 17 and 18 are sectional views showing a first electromagnetic valve used in the device shown in FIG. 16;

FIGS. 19 and 20 are sectional views showing a second electromagnetic valve used in the device shown in FIG. 16;

FIGS. 22A to 22L are timing charts for explaining the operation of the circuit shown in FIG. 21.

DETAILED DESCRIPTION OF THE PREFERRED EMBODIMENTS

The preferred embodiments of the present invention will now be described sequentially with reference to the accompanying drawings.

Figure 1:
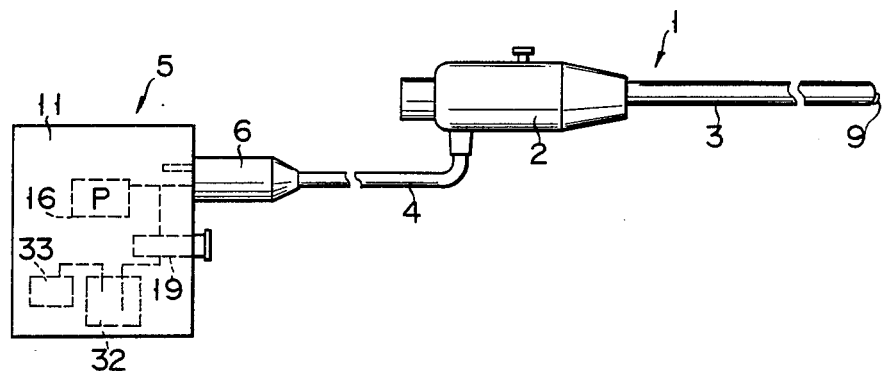
FIG. 1 is a side view schematically showing an endoscope and a liquid supplying device according to a first embodiment of the present invention.
Figure 2:
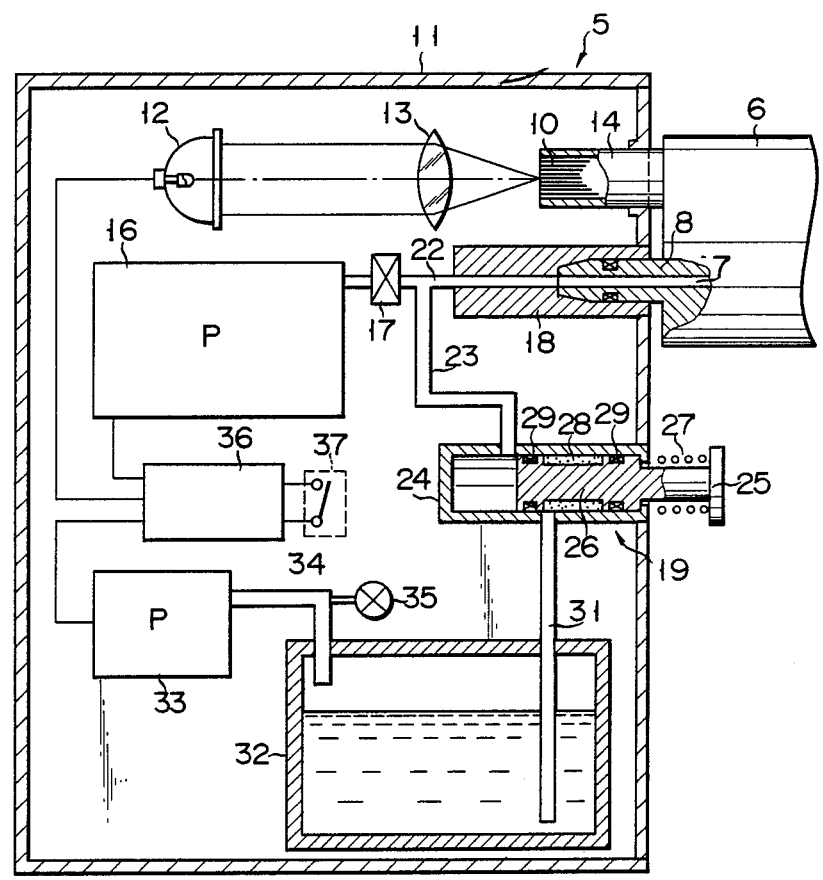
FIG. 2 is a sectional view showing details of the device shown in FIG. 1.
Figure 3:
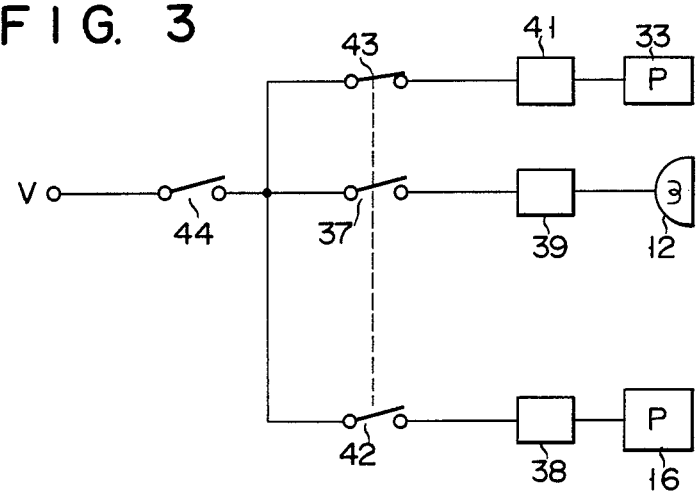
FIG. 3 is a circuit diagram of the device shown in FIG. 2.

FIGS. 1 to 3 show the first embodiment of the present invention. Referring to FIG. 1, reference numeral 1 denotes an endoscope which has a control section 2 and an insertion section 3 extending from the section 2. One end of a universal cord 4 is connected to the control section 2 and the other end is connected to a connector 6 to be connected to a liquid supplying device 5. An air supply channel 7 and a light guide 10 extend within the endoscope 1 and the universal cord 4. One end of the air supply channel 7 opens to the distal end of a connecting mouthpiece 8 of the connector 6, as shown in FIG. 2. The other end of the air supply channel 7 is connected to a nozzle 9 arranged at the distal end of the insertion section 3. The liquid supplying device 5 to which the connector 6 is to be connected has the construction as shown in FIG. 2. More specifically, the device 5 has a housing 11 and a light source 12 arranged therein. Light emitted from the light source 12 is converged by a lens 13 and becomes incident on the light guide 10 inside a light guide mouthpiece 14 formed at the end face of the connector 6. The light guide 10 extends through the universal cord 4, the control section 2, and the insertion section 3 to reach the distal end of the insertion section 3. An air pump 16 is also arranged in the housing 11. A check valve 17 is connected to the delivery side of the pump 16. Pipes 22 and 23 are connected to the check valve 17. The pipe 22 is connected to a receptacle 18 which is fixed to the housing 11 and which receives the connecting mouthpiece 8 of the connector 6. The pipe 23 is connected to a cylinder 24 of a switching mechanism 19 described below. The switching mechanism 19 has a cylinder 24 fixed to the housing 11, a piston 26 which is slidably inserted in the cylinder 24 and has at one end thereof a control button 25 extending outside the housing 11, and a spring 27 for biasing the piston 26 in the direction projecting from the cylinder 24. An annular groove 28 is formed in the outer surface of the piston 26. O-rings 29 are arranged on the outer surface of the piston 26 to provide a good hermetic seal between the piston 26 and the cylinder 24. The spring 27 normally biases the piston 26 to a first position (standby position) shown in FIG. 2. The pipe 23 is connected to the side wall of the cylinder 24 so as to communicate with the interior of the cylinder 24 when the piston 26 is at the first position. One end of a lifting pipe 31 is connected to the cylinder 24 to communicate with the annular groove 28. The other end of the lifting pipe 31 is hermetically inserted inside a liquid supply tank 32 holding a liquid therein. Therefore, when the piston 26 is at the first position, it blocks communication between the pipe 23 and the lifting pipe 31. However, when the piston 26 is pushed to a second position, it allows communication between the pipe 23 and the lifting pipe 31 through the annular groove 28.

Another air pump 33 for liquid supply (may also be referred to as a liquid supply pump 33 hereinafter) is also arranged inside the housing 11. The air pump 33 communicates with the upper space inside the liquid supply tank 32 through a pipe 34 so as to supply compressed air thereinto. A relief valve 35 is arranged at an intermediate position of the pipe 34.

A control circuit 36 is assembled in the liquid supplying device 5. The control circuit 36 controls the light source 12 and the pumps 16 and 33. A lamp switch 37 is connected to the control circuit 36 and can be externally operated.

FIG. 3 shows a circuit diagram of the liquid supplying device. The pump 16 is controlled by an air pump driver 38, the light source 12 is controlled by a lamp driver 39, and the liquid supply pump 33 is controlled by a liquid supply pump driver 41. Inputs are supplied to the drivers 38, 39 and 41 through the lamp switch 37, an air supply switch 42, and a liquid supply switch 43, respectively. These drivers 38, 39 and 41 are connected to a power supply through a power switch 44.

The various operation modes of the liquid supplying device having the construction as described above will now be described. When diagnosis is to be performed, the lamp switch 37 is turned on. Then, the air supply switch 42 is turned on. When the power switch 44 is turned on, the light source 12 is turned on, and the air pump 16 is actuated. Then, diagnosis with the endoscope 1 can be performed. During diagnosis, the liquid supply switch 43 is kept open, and air is not supplied.

In order to clean or disinfect the air supply channel 7 after using the endoscope 1, only the power switch 44 is turned on. Then, since only the liquid supply switch 42 is normally closed, only the liquid supply pump 33 is actuated. The liquid supply pump 33 supplies compressed air to the liquid supply tank 32 so as to decompress the liquid in the liquid supply tank 32 and to supply it to the lifting pipe 31. Note that the light source 12 is OFF during this operation. When the control button 25 of the switching mechanism 19 is pressed such that the piston 26 reaches the second position, the lifting pipe 31 and the pipes 22 and 23 communicate through the annular groove 28. Then, the liquid is supplied to the air supply channel 7 of the endoscope 1 through the receptacle 18, thereby cleaning and disinfecting the channel 7. When the lamp switch 37 is closed after this cleaning operation, the state before the diagnosis is established. The air pump 16 is then actuated to supply air into the channel 7 to dry it.

Therefore, when the light source 12 is ON in the device of the above construction, the liquid supply switch 43 is always open. In other words, the liquid supply tank 32 is not decompressed in this state. For this reason, even if the switching mechanism 19 is switched to the liquid supplying side or the second position, liquid is not supplied to the channel 7.

Figure 4:
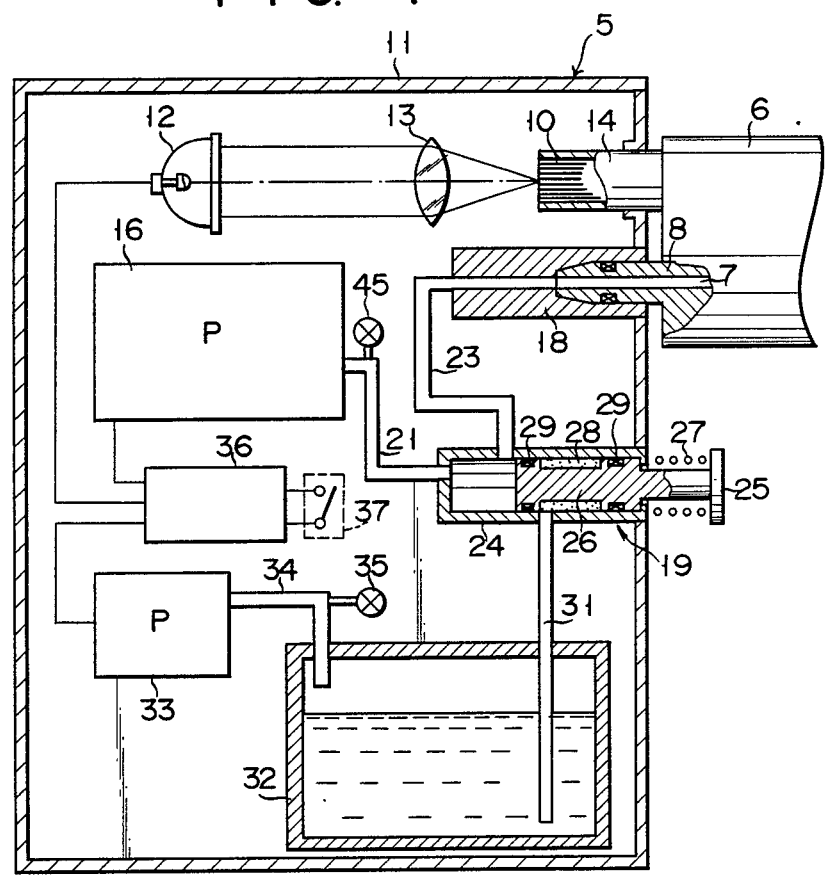
FIG. 4 is a sectional view showing a modification of the device shown in FIG. 2.
Figure 5:
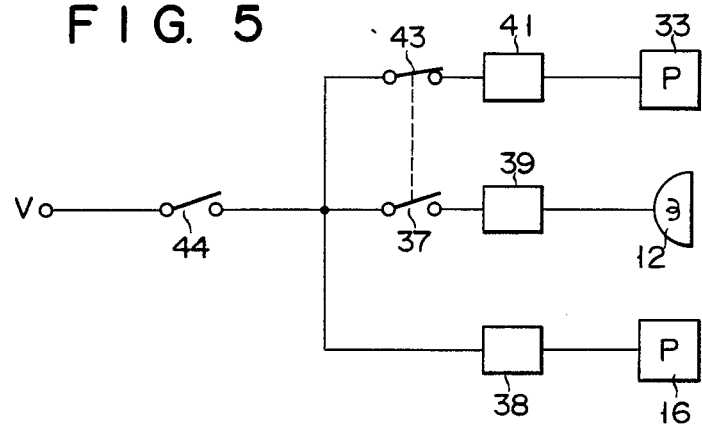
FIG. 5 is a circuit diagram of the device shown in FIG. 4.

In the embodiment described above, the air pump 16 is directly connected to the receptacle 18. However, as shown in FIG. 4, the air pump 16 can be connected to the space inside the cylinder 24 through a pipe 21. Then, the check valve 17 can be omitted. Note that reference numeral 45 denotes a relief valve. Furthermore, as shown in FIG. 5, the air supply switch 42 can be omitted, and the power switch 44 can be directly connected to the air pump driver 38.

Figure 6:
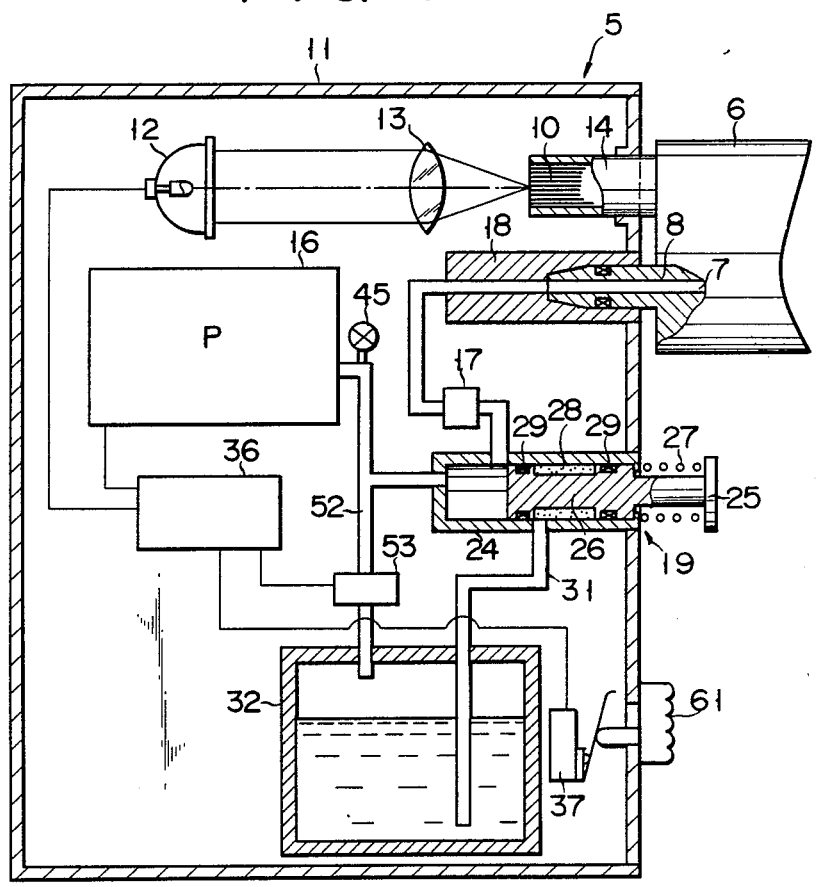
FIG. 6 is a sectional view of a liquid supplying device according to a second embodiment of the present invention.
Figure 7:
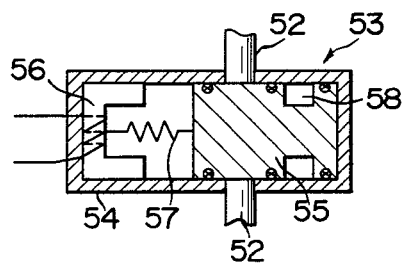
FIG. 7 is a sectional view of a direction control valve used in the device shown in FIG. 6.
Figure 8:
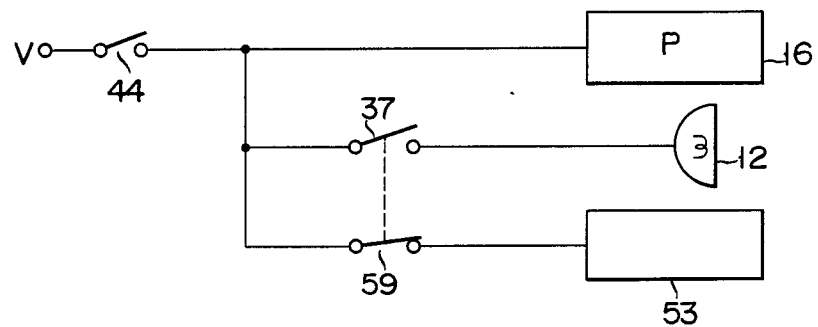
FIG. 8 is a circuit diagram of the device shown in FIG. 6.

FIGS. 6 to 8 show a second embodiment of the present invention. The device of this embodiment has only one air pump 16. The air pump 16 is connected to a liquid supply tank 32 through a pipe 52. A selector valve 53 is arranged at an intermediate position along the pipe 52. The pipe 52 is also connected to a cylinder 24 of a switching mechanism 19. The valve 53 has a construction as shown in FIG. 7. Referring to FIG. 7, the valve 53 has a cylinder 54 and a piston 55 arranged inside the cylinder 54. The piston 55 is actuated by a solenoid 56. The piston 55 is biased by a spring 57 to a first position (standby position) shown in FIG. 7. When the solenoid 56 is energized, it attracts the piston 55 by a given distance. When the piston 55 is at the first position, it blocks the pipe 52. When the solenoid 56 is energized and the piston 55 moves, the pipe 52 is communicated through an annular groove 58 formed in the outer surface of the piston 55.

In a control circuit 36 of this embodiment, a switch 59 for allowing communication between the selector valve 53 and the solenoid 56 operates in an opposite manner, as shown in FIG. 8 to the lamp switch 37. More specifically, when the lamp switch 37 is open, the switch 59 is closed, and when the lamp switch 39 is closed, the switch 59 is open.

The lamp switch 37 is operated by a sliding button 61. The air pump 16 is directly connected to a power switch 44.

When diagnosis is to be performed according to this embodiment, the lamp switch 37 is closed by operating the sliding button 61. Then, the switch 59 of the selector valve 53 is opened, and the valve 53 is kept closed. Therefore, no compressed air is supplied to the liquid supply tank 32 by the air pump 16. For this reason, even if the switching mechanism 19 is accidentally set to the liquid supplying side during diagnosis, liquid will not be supplied to the air supply channel 7 through a lifting pipe 31.

In order to clean the air supply channel 7, the lamp switch 37 is opened. Then, in synchronism with this, the switch 59 is closed and the solenoid 56 of the valve 53 is energized. Then, the piston 55 is attracted to the solenoid 56, so that the valve 53 is opened, and the pipe 52 is comunicated. Since the air pump 16 is actuated, compressed air from the pump is supplied to the liquid supply tank 32 to allow supply of a liquid held therein.

When the switching mechanism 19 is operated in this state, the liquid in the tank 32 flows into the air supply channel 7 to clean it.

In order to dry the channel 7, the lamp switch 37 is turned on. Then, the compressed air in the air pump 16 is supplied to the air supply channel 7 through the cylinder 24 of the switching mechanism 19. At this time, the valve 53 is closed. During this drying process, air can also be supplied when the lamp switch 37 is open. Therefore, the piston 25 of the switching mechanism 19 can be switched to the first position when the lamp switch 37 is open.

FIG. 9 shows a third embodiment of the present invention. In this embodiment, the selector valve 53 of the second embodiment is arranged at an intermediate position of the lifting pipe 31 between the switching mechanism 19 and the liquid supply tank 32. Other details of the construction of the third embodiment remain the same as those of the second embodiment. The device of the third embodiment operates in the same manner as the second embodiment.

Figure 10:
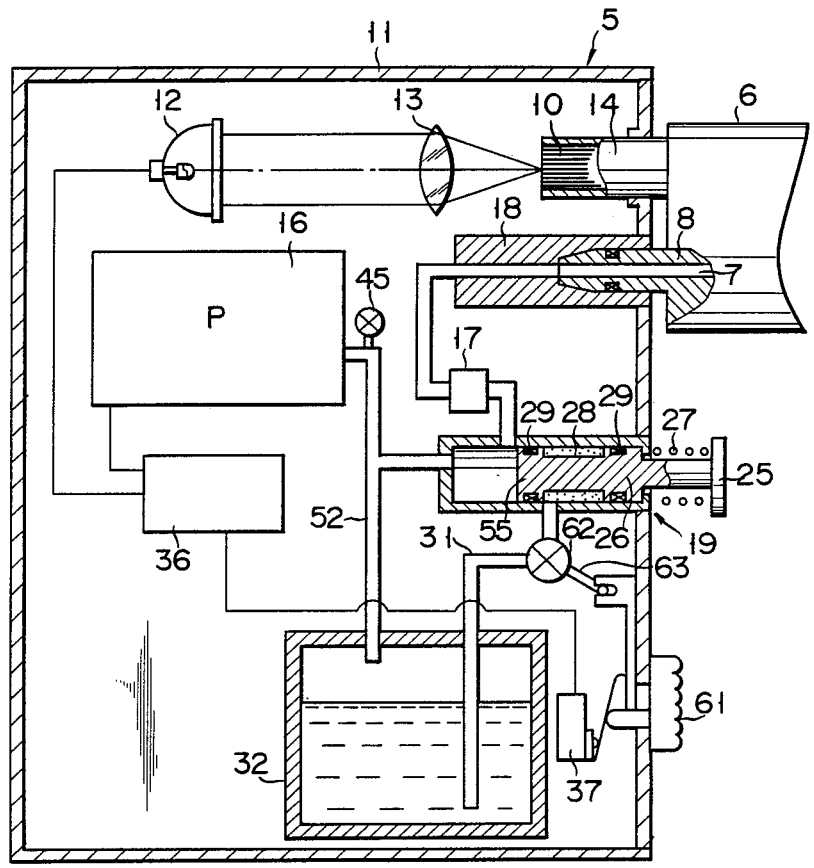
FIG. 10 is a sectional view showing a liquid supplying device according to a fourth embodiment of the present invention.
Figure 11:
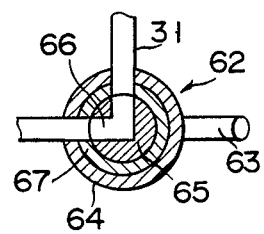
FIG. 11 is a sectional view of a direction control valve used in the device shown in FIG. 10.

FIGS. 10 and 11 show a fourth embodiment of the present invention. The fourth embodiment has substantially the same construction as that of the third embodiment and is different therefrom only in that a manual selector valve 62 is arranged at an intermediate position of the lifting pipe 31 in place of the valve 53 of the third embodiment. The valve 62 engages with the sliding button 61 for operating the lamp switch 37 through a lever 63 and is opened/closed in synchronism with the sliding button 61. As shown in FIG. 11, the valve 62 has a cylindrical valve body 64 and a valve plug 65 rotatably arranged therein. The valve plug 65 has a channel 66 for allowing communication with the lifting pipe 31. The lever 63 extends from the valve plug 65 outside the valve body 64. The channel 66 is opened/closed by rotating the valve plug 65 by means of the lever 63. An elastic member 67 for providing a hermetic seal is arranged around the valve plug 65. When the sliding button 61 is operated and the lamp switch 37 is closed, the selector valve 62 is closed through the lever 63 coupled to the sliding button 61. The valve 62 is opened as the lamp switch 37 is opened. Other details of the operation of this embodiment are the same as those of the second embodiment. Note that the selector valve 62 can be inserted at an intermediate position of the pipe 52.

Figure 12:
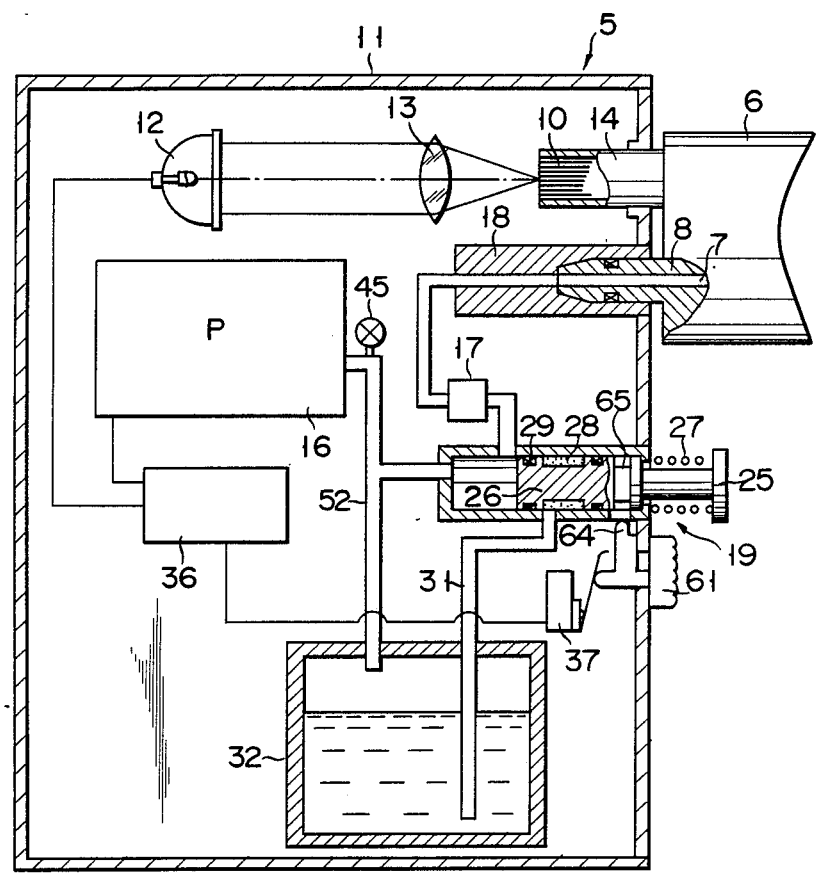
FIG. 12 is a sectional view of a liquid supplying device according to a fifth embodiment of the present invention.

FIG. 12 is a fifth embodiment of the present invention. This embodiment does not have a selector valve 53 or 62 but has a locking mechanism for locking the piston 26 of the switching mechanism 19 by means of the sliding button 61. This locking mechanism has a stopper pin 64 formed on the sliding button 61, and a stopper groove 65 formed on the outer surface of the piston 26 of the switching mechanism 19. When the sliding button 61 is operated while the piston 26 is at the first position, the stopper pin 64 is fitted in the stopper groove 65 so as to lock the piston 26 at the first position and the lamp switch 37 is closed. Thus, if the lamp switch 37 is closed, the switching mechanism 19 is locked and liquid cannot be supplied. However, when the lamp switch 37 is open, that is, when the sliding button 61 is not being operated, the switching mechanism 19 can be operated and the air pump 16 is operative. Therefore, liquid can be supplied to clean the air supply channel 7.

Figure 13:
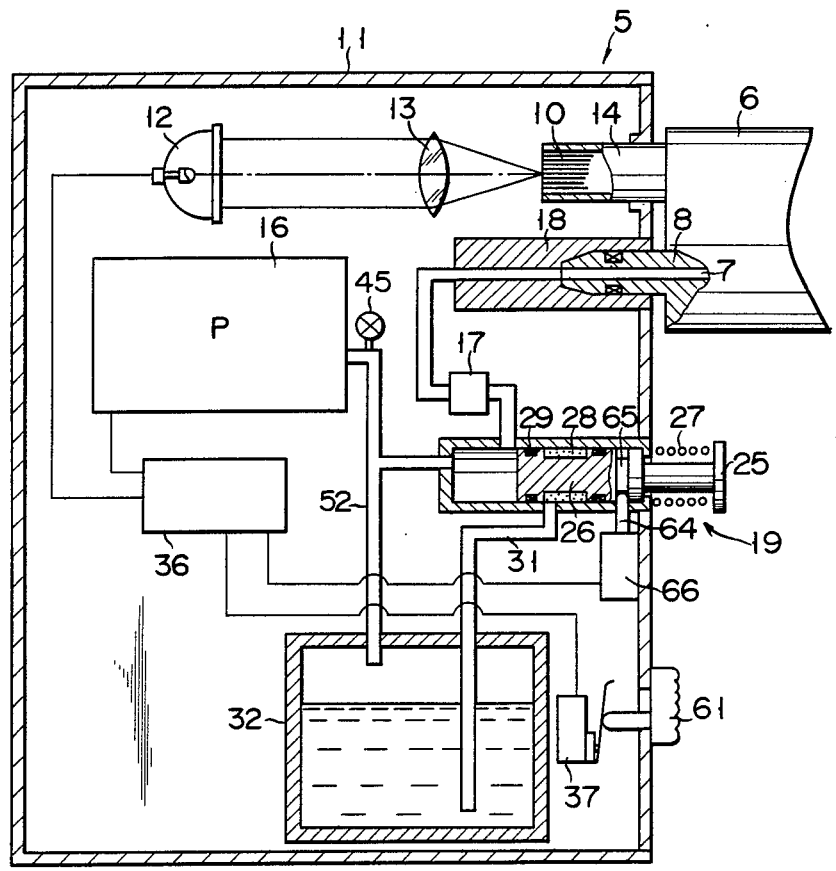
FIG. 13 is a sectional view of a liquid supplying device according to a sixth embodiment of the present invention.

FIG. 13 shows a sixth embodiment of the present invention. In this embodiment, instead of operating the stopper pin 64 by means of the sliding button 61, the stopper pin 64 is operated by a solenoid 66. The solenoid 66 is energized by the control circuit 36 to project the stopper pin 64, as needed. Thus, when the lamp switch 37 is closed, the solenoid 66 is energized. Other details of this embodiment remain the same as those of the fifth embodiment.

Figure 14:
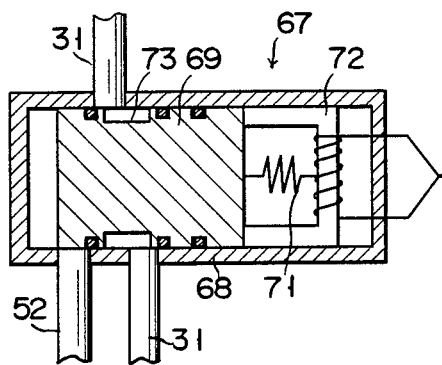
FIGS. 14 and 15 are sectional views showing a direction control valve as a switching mechanism.
Figure 15:
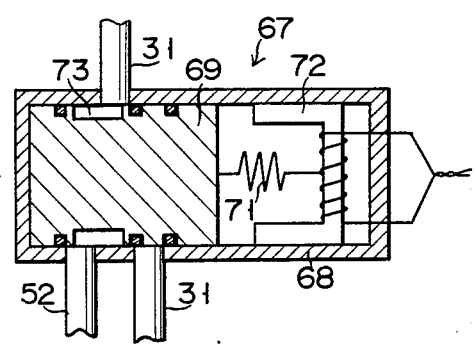
Figure 16:
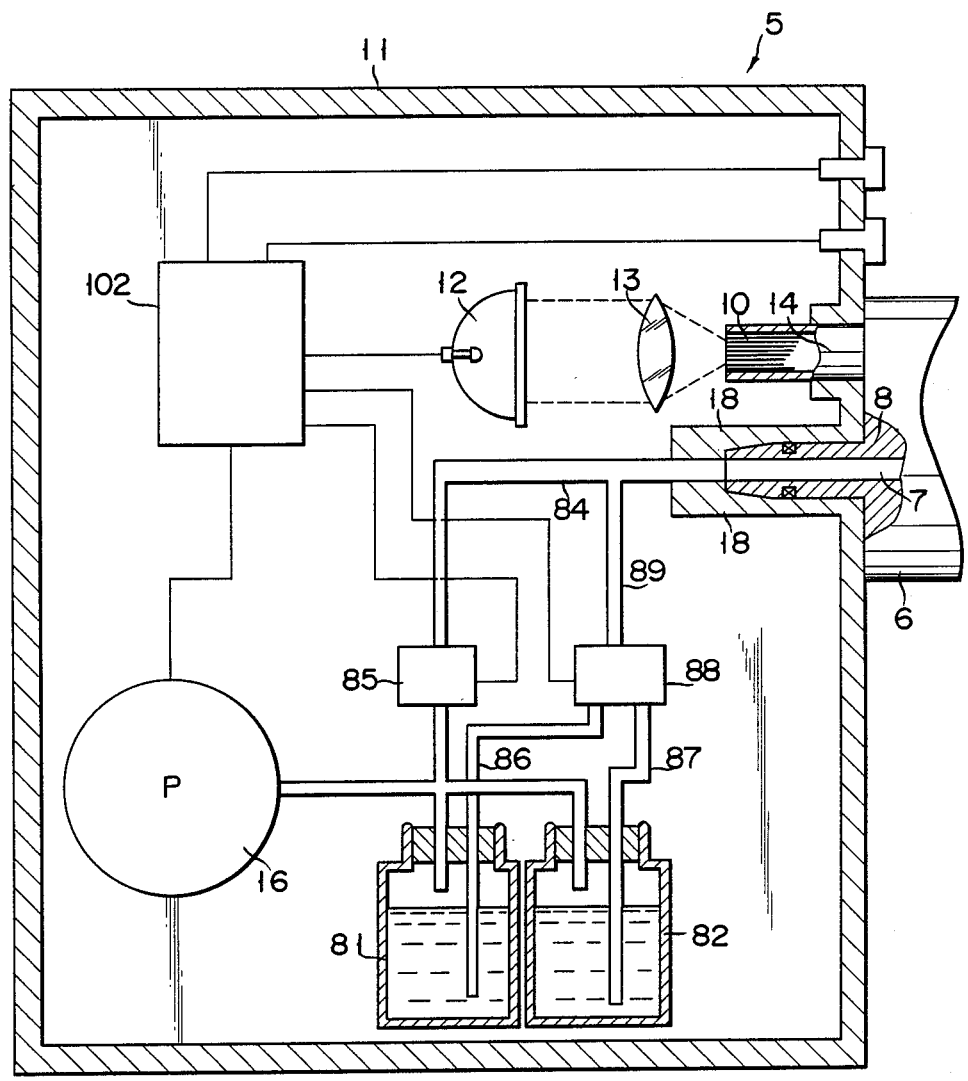
FIG. 16 is a sectional view of a liquid supplying device according to a seventh embodiment of the present invention.

A selector valve 67 as shown in FIGS. 14 and 15 can be used as the switching mechanism 19. The valve 67 has a cylinder 68, a piston 69 slidably inserted in the cylinder 68, a spring 71 for biasing the piston 69 from a second position shown in FIG. 14 to a first position shown in FIG. 15, and a solenoid 72 for attracting the piston 69 to the second position. When the lamp switch 37 is open, that is, when the light source 12 is not ON, the solenoid 72 is energized and the piston 69 is attracted to the second position. Then, the lifting pipe 31 communicates through an annular groove 73 formed in the outer surface of the piston 69. However, when the lamp switch 37 is closed, the solenoid 72 is not energized. Thus, the piston 69 is at the first position and allows communication of the air supply pipe 52. In this state, liquid cannot be supplied.

FIGS. 16 to 22 show a seventh embodiment of the present invention. In this embodiment, two types of liquid supply tanks 81 and 82 are arranged. An infusion solution or a disinfectant is held in the tank 81, and water is held in the tank 82. The air pump 16 and the receptacle 18 are coupled through an air supply pipe 84. A first electromagnetic valve 85 is arranged at an intermediate position of the air supply pipe 84. Lifting pipes 86 and 87 are respectively connected to the liquid supply tanks 81 and 82. The pipes 86 and 87 are connected to the receptacle 18 through a second electromagnetic valve 88 and a liquid supply pipe 89. The tanks 81 and 82 also communicate with the air supply pump 16 and are supplied with compressed air to thereby supply the liquids.

The first electromagnetic valve 85 has the construction as shown in FIGS. 17 and 18. More specifically, a piston 92 is slidably inserted inside a cylinder 91 connected to the air supply pipe 84. The piston 92 is driven by a solenoid 93. The piston 92 is also biased by a spring 94 from a second position shown in FIG. 18 to a first position shown in FIG. 17. When the solenoid 93 is not energized, the piston 92 is at the first position and the air supply pipe 84 is allowed to communicate through an annular groove 95 formed in the outer surface of the piston 92. When the solenoid 93 is energized it attracts the piston 92 against the biasing force of the spring 94. Then the piston 92 blocks the air supply pipe 84.

The second electromagnetic valve 88 has the construction as shown in FIGS. 19 and 20. The valve 88 has a cylinder 96 which is connected to the lifting pipes 86 and 87 and to a liquid supply pipe 89, and a piston 97 which is slidably inserted in the cylinder 96. The piston 97 is moved by a solenoid 98 and a spring 99. When the solenoid 98 is not energized, the piston 97 is biased by the spring 99 to a first position (standby position) shown in FIG. 19. When the solenoid 98 is energized, the piston 97 is attracted by the solenoid 98 against the biasing force of the spring 99 and is moved to a second position shown in FIG. 20. When the piston 97 is at the first position, the lifting pipe 86 communicates with the liquid supply pipe 89 through an annular groove 101 formed in the outer surface of the piston 97, while the lifting pipe 87 is blocked by the outer surface of the piston 97. When the piston 97 is at the second position, the lifting pipe 87 communicates with the liquid supply pipe 89 through the annular groove 101 of the piston 97 while the lifting pipe 86 is blocked.

Figure 21:
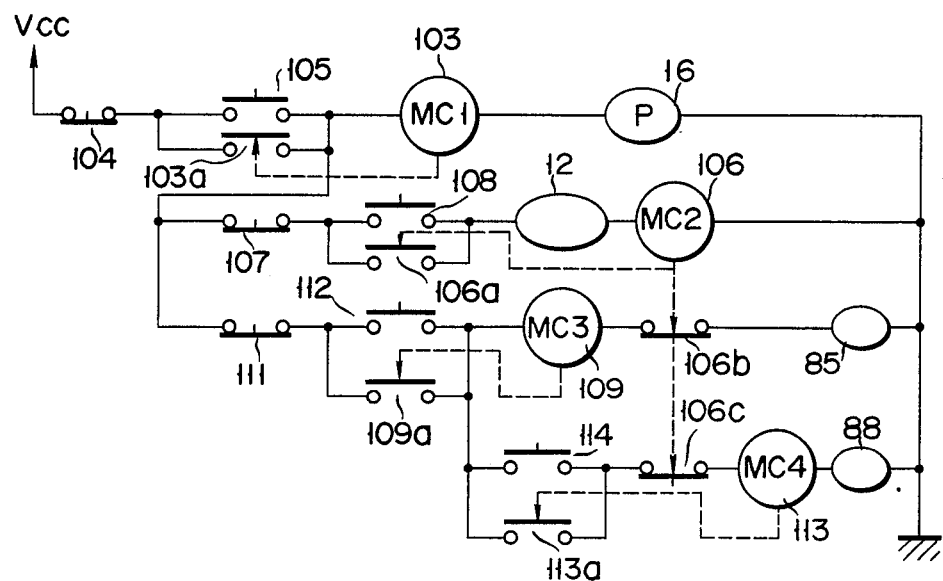
FIG. 21 is a circuit diagram of the device shown in FIG. 16.

The air pump 16, the first and second electromagnetic valves 85 and 88 and the light source 12 are connected in a control circuit 102, a circuit diagram of which is shown in FIG. 21. Various switches for controlling the control circuit 102 are arranged at the front side of the housing 11. In the control circuit 102, a drive voltage Vcc is applied to the series circuit of the air pump 16 and a first electromagnetic contactor 103 through a normally closed main stop switch 104 and a normally open main switch 105. A contact 103a of the contactor 103 is connected in parallel with the main switch 105. The drive voltage Vcc is applied to a series circuit of the light source 12 and a second electromagnetic contactor 106 through the main stop switch 104, the main switch 105, a normally closed lamp stop switch 107 and a normally open lamp switch 108. A contact 106a of the contactor 106 is connected in parallel with the lamp switch 108. The drive voltave Vcc is also applied to a series circuit of the first electromagnetic valve 85, a third electromagnetic contactor 109 and a contact 106b of the contactor 106 through the main stop switch 104, the main switch 105, a normally closed cleaning stop switch 111, and a normally open liquid supply switch 112. A contact 109a of the contactor 109 is conneced in parallel with the liquid supply switch 112. A series circuit of the second electromagnetic valve 88, a fourth electromagnetic contactor 113 and a contact 106c of the contactor 106 is connected through a normally open switch 114 to a node between the switch 112 and the contactor 109. A contact 113a of the contactor 113 is connected in parallel with the switch 114.

The operation of this embodiment is performed in accordance with the timing chart shown in FIGS. 22A to 22L. When the main switch 105 is closed, the drive voltage Vcc is applied to the air pump 16 which starts operating. Then, the first electromagnetic contactor 103 is energized to close its contact 103a. Thus, the operation of the air pump 16 is continued. The delivery pressure of the air pump 16 is applied to the liquid supply tanks 81 and 82 to decompress the liquids held therein. However, since the first and second electromagnetic valves 85 and 88 are closed, the liquids will not be supplied from these tanks 81 and 82.

A case for cleaning the air supply channel 7 of the endoscope 1 will now be described. First, when the liquid supply switch 112 is closed, the third electromagnetic contactor 109 is energized and its contact 109a is closed. Then, the first electromagnetic valve 85 is energized, and the piston 92 moves to the second position shown in FIG. 18 to block the air supply pipe 84. Thus, supply of air to the air supply channel 7 is not performed. Since the piston 97 of the second electromagnetic valve 88 is at the first position shown in FIG. 19, the lifting pipe 86 communicating with the tank 81 holding the infusion solution therein communicates with the liquid supply pipe 89. However, the lifting pipe 87 is blocked. Therefore, only the infusion solution is supplied to the air supply channel 7.

When the switch 114 is operated and closed, the fourth electromagnetic contactor 113 is energized and its contact 113a is closed. Then, the valve 88 is energized, and the piston 97 moves to the second position shown in FIG. 20. The lifting pipe 87 communicates with the liquid supply pipe 89, and the lifting pipe 86 is blocked by the piston 97. Therefore, only the water in the tank 32 is supplied to the air supply channel 7 of the endoscope 1, thus cleaning it with water.

When the cleaning stop switch 111 is despressed, the whole cleaning operation is stopped. More specifically, the valve 85 is returned to the first position shown in FIG. 17 and the second valve 88 is returned to the first position shown in FIG. 19. No liquid is supplied in this state.

Meanwhile, when the piston 92 of the first electromagnetic valve 85 returns to the first position, air is supplied to dry the air supply channel 7. The main stop switch 104 is then depressed to stop conduction of the first electromagnetic contactor 103 and to open its contact 103a. Then, the air pump 83 is deactivated, and the supply of air is stopped.

When diagnosis is to be performed with the endoscope 1, the main switch 105 and the lamp switch 108 are turned on. In this case, the second electromagnetic contactor 106 is energized and its contact 106a is closed. Power is supplied to turn on the light source 12. When the contact 106a of the contactor 106 is closed, the light source 102 is kept ON. However, at the same time, contacts 106b and 106c are opened. Therefore, the solenoids 93 and 98 for the first and second electromagnetic valves 85 and 88 are not energized. That is, when the light source 12 is ON, the valves 85 and 88 are OFF and erroneous supply of liquid is prevented.

The means for detecting the ON/OFF state of the light source can be a current detector for detecting a current flowing to the light source or a photosensor for detecting light emitted from the light source according to the present invention.

Figure 23:
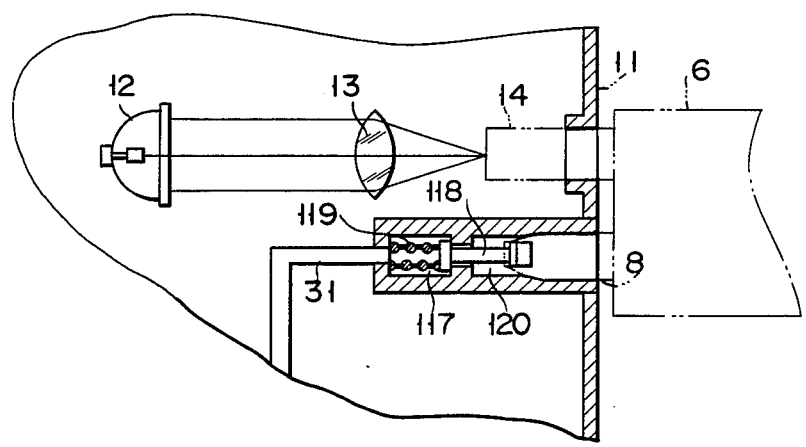
FIG. 23 is a sectional view showing a modification of a receptacle according to the present invention.

The receptacle 18 can have a check valve 117, as shown in FIG. 23. A valve plug 118 is biased by a spring 119. When the connecting mouthpiece 8 of the connector 6 is not inserted, a channel 120 can be blocked. When the connecting mouthpiece 8 is inserted in the receptacle 18, the valve plug 118 is pressed through the mouthpiece to communicate the channel 120. Then, even if liquid is supplied while the connector 6 is removed, leakage of the liquid through the receptacle 18 is prevented.

As described above in detail, according to the present invention, accidental supply of an infusion solution or the like which may be harmful to the human body into a body cavity of a patient during diagnosis with an endoscope can be prevented. A liquid supplying device of the present invention does not require switching of connectors and the like and is easy to handle.

What is claimed is:

1. A liquid supplying device for an endoscope which includes a control section, an insertion section extended from the control section and having a nozzle at its distal end, a light guide cable extended from the control section and having a connector at its distal end, an air supply channel extending in the endoscope and having one end communicating with the nozzle and the other end opening to the connector, and a light guide extending in the endoscope from the distal end of the insertion section to the connector; said liquid supplying device comprising:

a housing with a connecting portion to which the connector of the endoscope is connected;

air and liquid supplying means, arranged inside the housing, for supplying liquid and air into the air supply channel from the other end of the air supply channel;

a light source which is arranged inside the housing and which emits light which becomes incident on the light guide from that end of the light guide which is near the connector; and regulating means for preventing the air and liquid supplying means from supplying liquid while the light source is ON.

2. A device according to claim 1, wherein said air and liquid supplying means includes a liquid supply tank holding liquid therein; an air pump; communicating means having an air supply pipe connecting the air pump to the connecting portion and liquid supply tank and a liquid supply pipe connecting the liquid supply tank to the connecting portion; and switching means which is connected to the communicating means and which is switched between a first position for allowing supply of air from the air pump to the air supply channel of the endoscope and a second position for allowing the supply of the liquid from the liquid supply tank to the air supply channel.

3. A device according to claim 2, wherein said regulating means includes a selector valve which is connected to the air supply pipe at a position between the air pump and the liquid supply tank and can be switched between a first position for blocking the air supply pipe and a second position for communicating the air supply pipe; a light source switch; and a control circuit which is connected to the selector valve, the light source switch, the light source, and the air pump, and which drives the air pump and light source and switches the selector valve to the first position when the light source switch is closed, and which switches the selector valve to the second position when the light source switch is open.

4. A device according to claim 3, wherein said selector valve has a cylinder connected to the air supply pipe; a piston which is arranged inside the cylinder to be movable between a first position for blocking communication of the air supply pipe and a second position for allowing communication of the air supply pipe; a biasing member for biasing the piston to the first position; and a solenoid which is arranged inside the cylinder and which is energized by the control circuit to attract the piston to the second position when the light source switch is open.

5. A device according to claim 2, wherein said regulating means includes a selector valve which is connected to the liquid supply pipe at a position between the switching means and the liquid supply tank and which can be switched between a first position to block communication of the liquid supply pipe and a second position for allowing communication of the liquid supply pipe; a light source switch; and a control circuit which is connected to the selector valve, the light source switch, the light source, and the air pump, and which drives the air pump and light source and switches the selector valve to the first position when the light source switch is closed, and which switches the selector valve to the second position when the light source switch is open.

6. A device according to claim 5, wherein said selector valve has a cylinder connected to the liquid supply pipe; a piston which is arranged in the cylinder to be movable between a first position for blocking communication of the liquid supply pipe and a second position for allowing communication of the liquid supply pipe; a biasing member for biasing the piston to the first position; and a solenoid which is energized and attracts the piston to the second position when the light source switch is open.

7. A device according to claim 2, wherein said regulating means includes a light source switch; a control member which is engaged with the light source switch and which is mounted on the housing to be movable between a first position for opening the light source switch and a second position for closing the light source switch; a control circuit which is connected to the light source switch, the light source, and the air pump and which drives the air pump and light source when the light source switch is closed; and a selector valve which is connected to the liquid supply pipe at a position between the switching means and the liquid supply tank, is engaged with the control member, and cooperates with the control member to allow communication of the liquid supply pipe when the control member is at the first position and to block communication of the liquid supply pipe when the control member is at the second position.

8. A device according to claim 2, wherein said regulating means includes a light source switch, a control member which is engaged with the light source switch and is mounted on the housing to be movable between a first position to open the light source switch and a second position to close the light source switch, and a control circuit which is connected to the light source switch, the light source and the air pump and drives the air pump and light source when the light source switch is closed; and the control member has a stopper which engages with the switching means to lock the switching means at the first position when the control member is at the second position.

9. A device according to claim 2, wherein said regulating means includes a light source switch; locking means for engaging with the switching means to lock the switching means at the first position; and a control circuit which is connected to the light source switch, the air pump and the light source, and which drives the air pump and light source and engages the locking means with the switching means when the light source switch is closed and which disengages the locking means from the locking means when the light source switch is open.

10. A device according to claim 9, wherein said locking means has a solenoid connected to the control circuit; and a plunger driven by the solenoid and engaged with the switching means.

11. A device according to claim 1, wherein said air and liquid supplying means includes a first air pump, a liquid supply tank holding a liquid therein, a second air pump connected to the liquid supply tank for decompressing the liquid held in the liquid supply tank, communicating means having an air supply pipe connecting the first air pump and the connecting portion and a liquid supply pipe connecting the liquid supply tank and the air supply pipe, and switching means which is connected to the communicating means and which is movable between a first position for allowing supply of air from the first air pump to the air supply channel of the endoscope and a second position for allowing supply of the liquid decompressed by the second air pump to the air supply channel; and said regulating means has a light source switch, and a control circuit which is connected to the light source switch, the first and second air pumps and the light source, and which drives the first air pump and light source when the light source switch is closed and which drives the second air pump when the light source switch is open.

12. A device according to claim 1, wherein said air and liquid supplying means includes first and second liquid supply tanks holding liquid therein, an air pump, an air supply pipe connecting the air pump to the connecting portion and the first and second liquid supply tanks, a liquid supply pipe connecting the first and second liquid supply tanks to the connecting portion, a first selector valve which is connected to the air supply pipe at a position between the air pump and the connecting portion and which is movable between a first position for allowing supply of air from the air pump to the connecting portion and a second position for allowing supply of air from the air pump into the first and second liquid supply tanks, and a second selector valve which is connected to the liquid supply pipe at a position between the first and second liquid supply tanks and the connecting portion, and which can be switched between a first position for allowing supply of the liquid in the first liquid supply tank to the connecting portion and a second position for allowing supply of the liquid in the second liquid supply tank to the connecting portion; and said regulating means includes a light source switch, and a control circuit which is connected to the air pump, the light source, and the light source switch, and which drives the air pump and light source and switches the first and second selector valves to the first positions, respectively, when the light source switch is closed, and which allows the first and second selector valves to be switched to the second positions, respectively, when the light source switch is open.

* * * * *

UNITED STATES PATENT AND TRADEMARK OFFICE
CERTIFICATE OF CORRECTION

PATENT NO. : 4,550,716
DATED : November 5, 1985
INVENTOR(S) : Kunio Kinoshita

It is certified that error appears in the above—identified patent and that said Letters Patent are hereby corrected as shown below:

Title page:

[73] Assignee: OLYMPUS OPTICAL CO.,LTD.

Signed and Sealed this

Twenty-third Day of September 1986

[SEAL]

Attest:

DONALD J. QUIGG

Attesting Officer

Commissioner of Patents and Trademarks